US006197510B1

(12) United States Patent
Vinayagamoorthy

(10) Patent No.: US 6,197,510 B1
(45) Date of Patent: Mar. 6, 2001

(54) MULTI-LOCI GENOMIC ANALYSIS

(75) Inventor: Thuraiayah Vinayagamoorthy, Saskatoon (CA)

(73) Assignee: Bio-Id Diagnostic Inc., Saskatoon (CA)

( * ) Notice: Subject to any disclaimer, the term of this patent is extended or adjusted under 35 U.S.C. 154(b) by 0 days.

(21) Appl. No.: 09/165,264

(22) Filed: Oct. 1, 1998

(51) Int. Cl.$^7$ .............................. C12P 19/34; C12Q 1/70
(52) U.S. Cl. .................. 435/6; 435/91.2; 435/5
(58) Field of Search .................. 435/6, 91.2, 5

(56) References Cited

U.S. PATENT DOCUMENTS

| 4,683,195 | 7/1987 | Mullis et al. ............... 435/6 |
| 4,683,202 | 7/1987 | Mullis et al. ............... 435/91 |
| 4,965,188 | 10/1990 | Mullis et al. ............... 435/6 |
| 5,403,707 | 4/1995 | Atwood et al. ............... 435/5 |
| 5,552,283 | 9/1996 | Diamandis et al. ............... 435/6 |
| 5,582,989 | 12/1996 | Caskey et al. ............... 435/6 |
| 5,776,737 | 7/1998 | Dunn ............... 435/91.1 |

FOREIGN PATENT DOCUMENTS

| WO 93/06243 | 4/1993 | (WO) . |
| WO 94/10315 | 5/1994 | (WO) . |
| WO 98/26095 | 6/1998 | (WO) . |
| WO 99/29900 | 6/1999 | (WO) . |

OTHER PUBLICATIONS

Li et al., "Direct electrophoretic detection of the allelic states of single DNA molecules in human sperm by using the polymerase chain reaction" Proc. Natl. Acad. Sci USA vol. 87, pp. 4580–4584, 1990.*

Rawn, "Biochemistry" pp. 666, 708, Carolina Biological Supply, North Carolina 1989.*

S. C. Roemer et al., Simultaneous Bi-Directional Cycle Sequencing, LI-COR Virtual Poster Session [on-line], September 1997. retrieved on Sep. 4, 1998, from Internet: <URL:http://www.licor.com/bio/Posters/GenSeq97/GenSeq97.htm>.

D.L. Steffens et al., Multiplex Amplification of Human STR Loci using Infrared Fluorescence Detection, LI-COR Virtual Poster Session [on-line], Feburary, 1997.

Visible Genetics Inc., Application Note, HPV Genotyping using the OpenGene Automated DNA Sequencing System, Jan. 16, 1998.

Visible Genetics Inc., Application Note, HPV Genotyping using the OpenGene Automated DNA Sequencing System, Jan. 16, 1998.

Visible Genetics Inc., Application Note, p53 Mutation Detection using the OpenGene Automated DNA Sequencing System, May 3, 1998.

Jones, Leslie B. et al.: "Octamer-primed cycle sequencing using dye-terminator chemistry" Nucleic Acids Research, vol. 26, No. 11, 1998, pp. 2824–2426, XP002131455.

Horton, Joseph H.: "Optimized Conditions for Cycle Sequencing of PCR Products" PCR Methods And Applications, vol. 3, 1994, pp. 359–360, XP002131456.

White, Michael J. et al.: "Concatemer Chain Reaction: A Taq DNA Polymerase-Mediated Mechanism for Generating Long Tandemly Repetitive DNA Sequences" Analytical Biochemistry, US, Academic Press, San Diego, CA, vol. 199, No. 2, Dec. 1, 1991, pp. 184–190, XP000236491.

Kretz, Keith et al.: "Cycle Sequencing" PCR Methods & Applications, US, Cold Spring Harbor Laboratory Press, vol. 3, No. 5, Apr. 1, 1994, pp. S107–S112, XP000606764.

Sanger, F. et al.: "DNA Sequencing with Chain-Terminating Inhibitors" Proceedings of the National Academy of Sciences of the USA, US, New York, NY, vol. 74, No. 12, Dec. 1, 1977, pp. 5463–5467, XP000603873.

\* cited by examiner

*Primary Examiner*—Ardin H. Marschel
*Assistant Examiner*—Jeffrey S. Lundgren

(57) ABSTRACT

The invention provides a method of sequencing a nucleic acid in a reaction mixture comprising first and second nucleic acid target sequences. The target sequences may be present on the same or different nucleic acid molecules. First and second labelled sequencing primers are provided that are hybridizable, respectively, to the first and second nucleic acid target sequences. The second sequencing primer being at least as long as the total length of the first sequencing primer plus the length of the first target sequence. Each of the sequencing primer extension products beginning with the second sequencing primer will be longer than the primer extension products in the pool beginning with the first sequencing primer. Once the sequencing reactions have been completed, the lengths of the primer extension products in the pool may be detected by known methods, such as by gel electrophoresis.

12 Claims, 1 Drawing Sheet

SEQUENCE LISTING

```
<160> NUMBER OF SEQ ID NOS:  14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      Primer sequence

<400> SEQUENCE: 1
gtaggtagag tgaaacccgg                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      Primer sequence

<400> SEQUENCE: 2
cgggacctgg acttcatagc                                               20

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence:
      Primer sequence

<400> SEQUENCE: 3
gggggggggg gggggggggg gggggggggg gtaggtagag tgaaacccgg              50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence:
      Primer sequence

<400> SEQUENCE: 4
gggggggggg gggggggggg gggggggggg cgggacctgg acttcatagc              50

<210> SEQ ID NO 5
```

```
<211> LENGTH: 80
<212> TYPE: DNA
<213> ORGANISM: Artificial Sequence
<220> FEATURE:
<223> OTHER INFORMATION: Description of Artificial Sequence:
      Primer sequence

<400> SEQUENCE: 5
aaaaaaaaaa aaaaaaaaaa aaaaaaaaaa gggggggggg gggggggggg gggggggggg      60
gtaggtagag tgaaacccgg                                                  80

<210> SEQ ID NO 6
<211> LENGTH: 80
<212> TYPE: DNA
<213> ORGANISM: Artificial Sequence
<220> FEATURE:
<223> OTHER INFORMATION: Description of Artificial Sequence:
      Primer sequence

<400> SEQUENCE: 6
aaaaaaaaaa aaaaaaaaaa aaaaaaaaaa gggggggggg gggggggggg gggggggggg      60
cgggacctgg acttcatagc                                                  80

<210> SEQ ID NO 7
<211> LENGTH: 320
<212> TYPE: DNA
<213> ORGANISM: Artificial Sequence
<220> FEATURE:
<223> OTHER INFORMATION: Description of Artificial Sequence:
      Primer sequence

<400> SEQUENCE: 7
gggggggggg gggggggggg gggggggggg gggggggggg gggggggggg gggggggggg      60
gggggggggg gggggggggg gggggggggg gggggggggg gggggggggg gggggggggg     120
gggggggggg gggggggggg gggggggggg gggggggggg gggggggggg gggggggggg     180
gggggggggg gggggggggg gggggggggg gggggggggg gggggggggg gggggggggg     240
gggggggggg gggggggggg gggggggggg gggggggggg gggggggggg gggggggggg     300
aggctagcca tgcccttagt                                                 320

<210> SEQ ID NO 8
<211> LENGTH: 319
<212> TYPE: DNA
<213> ORGANISM: Artificial Sequence
<220> FEATURE:
<223> OTHER INFORMATION: Description of Artificial Sequence:
      Primer sequence

<400> SEQUENCE: 8
gggggggggg gggggggggg gggggggggg gggggggggg gggggggggg gggggggggg      60
gggggggggg gggggggggg gggggggggg gggggggggg gggggggggg gggggggggg     120
gggggggggg gggggggggg gggggggggg gggggggggg gggggggggg gggggggggg     180
gggggggggg gggggggggg gggggggggg gggggggggg gggggggggg gggggggggg     240
gggggggggg gggggggggg gggggggggg gggggggggg gggggggggg gggggggggg     300
tctgcagcac cctatcagg                                                  319

<210> SEQ ID NO 9
<211> LENGTH: 20
<212> TYPE: DNA
<213> ORGANISM: Artificial Sequence
```

-continued

```
<220> FEATURE:
<223> OTHER INFORMATION: Description of Artificial Sequence:
      Primer sequence

<400> SEQUENCE: 9
aggctagcca tgcccttagt                                                    20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
      Primer sequence

<400> SEQUENCE: 10
tctgcagcac cctatcagg                                                     19

<210> SEQ ID NO 11
<211> LENGTH: 320
<212> TYPE: DNA
<213> ORGANISM: Artificial Sequence
<220> FEATURE:
<223> OTHER INFORMATION: Description of Artificial Sequence:
      Primer sequence

<400> SEQUENCE: 11
gggggggggg gggggggggg gggggggggg gggggggggg gggggggggg gggggggggg        60
gggggggggg gggggggggg gggggggggg gggggggggg gggggggggg gggggggggg       120
gggggggggg gggggggggg gggggggggg gggggggggg gggggggggg gggggggggg       180
gggggggggg gggggggggg gggggggggg gggggggggg gggggggggg gggggggggg       240
gggggggggg gggggggggg gggggggggg gggggggggg gggggggggg gggggggggg       300
gcagattttg aagaaagaca                                                   320

<210> SEQ ID NO 12
<211> LENGTH: 318
<212> TYPE: DNA
<213> ORGANISM: Artificial Sequence
<220> FEATURE:
<223> OTHER INFORMATION: Description of Artificial Sequence:
      Primer sequence

<400> SEQUENCE: 12
gggggggggg gggggggggg gggggggggg gggggggggg gggggggggg gggggggggg        60
gggggggggg gggggggggg gggggggggg gggggggggg gggggggggg gggggggggg       120
gggggggggg gggggggggg gggggggggg gggggggggg gggggggggg gggggggggg       180
gggggggggg gggggggggg gggggggggg gggggggggg gggggggggg gggggggggg       240
gggggggggg gggggggggg gggggggggg gggggggggg gggggggggg gggggggggg       300
ttggtgtgtg taagccca                                                     318

<210> SEQ ID NO 13
<211> LENGTH: 320
<212> TYPE: DNA
<213> ORGANISM: Artificial Sequence
<220> FEATURE:
<223> OTHER INFORMATION: Description of Artificial Sequence:
      Primer sequence

<400> SEQUENCE: 13
gggggggggg gggggggggg gggggggggg gggggggggg gggggggggg gggggggggg        60
```

```
gggggggggg gggggggggg gggggggggg gggggggggg gggggggggg gggggggggg      120
gggggggggg gggggggggg gggggggggg gggggggggg gggggggggg gggggggggg      180
gggggggggg gggggggggg gggggggggg gggggggggg gggggggggg gggggggggg      240
gggggggggg gggggggggg gggggggggg gggggggggg gggggggggg gggggggggg      300
acgtggacga gggcatgccc                                                  320

<210> SEQ ID NO 14
<211> LENGTH: 320
<212> TYPE: DNA
<213> ORGANISM: Artificial Sequence
<220> FEATURE:
<223> OTHER INFORMATION: Description of Artificial Sequence:
      Primer sequence

<400> SEQUENCE: 14
gggggggggg gggggggggg gggggggggg gggggggggg gggggggggg gggggggggg       60
gggggggggg gggggggggg gggggggggg gggggggggg gggggggggg gggggggggg      120
gggggggggg gggggggggg gggggggggg gggggggggg gggggggggg gggggggggg      180
gggggggggg gggggggggg gggggggggg gggggggggg gggggggggg gggggggggg      240
gggggggggg gggggggggg gggggggggg gggggggggg gggggggggg gggggggggg      300
tgtgccatgt acagcagaga                                                  320
```

MULTI-LOCI GENOMIC ANALYSIS

FIELD OF THE INVENTION

The invention is in the field of nucleic acid analysis methods, including methods useful for sequence analysis and for diagnostic differentiation of cell types, such as identification of pathological organisms.

BACKGROUND OF THE INVENTION

A variety of methods are known for sequencing nucleic acids. Most DNA sequencing methods in current use are derived from the Sanger dideoxy chain-termination method (Sanger, F., S. Nicklen and A. R. Coulson (1977) "DNA sequencing with chain-terminating inhibitors" PNAS USA 74:5463–5467). These methods initiate polymerase catalysed duplication from a labelled primer complementary to a portion of the strand to be sequenced. Typically, four polymerase reactions are carried out, each with one of the four dideoxynucleotides (ddNTPs) mixed with the normal deoxynucleotides. The ddNTPs can not form a phosphodiester bond with subsequent nucleotides, so that in each reaction mixture chain polymerization is occasionally terminated at a ddNTP, producing a series of labelled strands whose lengths are indicative of the location of a particular base in the sequence. The resultant labelled fragments may be separated according to size by polyacrylamide gel electrophoresis. The position of the fragments in the gel may be determined by detecting the label, autoradiography may for example be used to detect radio-labelled fragments. Variations of the Sanger sequencing method have recently been adapted for large-scale automated sequencing using multiple fluorescent labels and capillary gel electrophoresis.

The polymerase chain reaction (PCR) may be used to amplify sequences prior to sequencing. Aspects of the PCR process are disclosed in the following United States patents: which are incorporated herein by reference: U.S. Pat. No. 4,683,195 issued Jul. 28, 1987 to Mullis et al. and U.S. Pat. No. 4,683,202 issued Jul. 28, 1987 to Mullis (see also U.S. Pat. No. 4,965,188; Saiki et al., (1988) Science 239:487–491; and, Mullis, K. B. et al. (eds.), 1994, "The Polymerase Chain Reaction", Springer Verlag, ISBN 0817637508). The PCR makes use of primers that anneal to opposite strands at either end of an intervening sequence in order to amplify the intervening sequence. Polymerase chain reaction mixtures are heated to separate complimentary strands between cycles of active polymerization. Under appropriate conditions, such cycles may result in a million-fold amplification of the target sequence. The amplified DNA may be then sequenced.

Nucleic acid amplification techniques may usefully be employed to detect a wide variety of pathogens or other organisms. Similarly, amplification of variable regions of a genome may be used to distinguish between one organism and another, a process sometimes called DNA fingerprinting. It is possible, however, to obtain a false-positive result from amplification reactions when non-specific amplification occurs. One approach to ameliorating this problem has been the use of multiple amplification reactions on a single sample, sometimes known as multiplex amplification, as for example disclosed in U.S. Pat. No. 5,582,989 issued Dec. 10, 1996 to Caskey et al., U.S. Pat. No. 5,552,283 issued to Diamandis et al. Sep. 3, 1996 and U.S. Pat. No. 5,403,707 issued Apr. 4, 1995 to Atwood et al. U.S (all of which are incorporated herein by reference). U.S. Pat. No. 5,582,989 teaches that the original PCR methods disclosed in the above-referenced patents to Mullis and Mullis et al. are not suitable for simultaneous multiplex amplification reactions. U.S. Pat. No. 5,403,707 teaches that it is useful in multiplexed amplification reactions to use primers that are very similar in length and therefore have similar melting temperatures.

Nucleic acid amplification techniques may be adapted and combined with sequencing reaction chemistry to provide sequence information. Such a system may be called 'cycle sequencing', and typically involves the use of a pair of primers, analogous to amplification primers, which anneal to opposite strands at either end of a sequence of interest. The usual amplification reaction chemistry is modified by including a chain-terminating nucleotide (such as a ddNTP) in the reaction mixture, so that some of the primer extension products will terminate at the places in the sequence of interest where that nucleotide occurs. However, some of the primer extension products will reach the opposite priming site, so that they may serve as the template for primer extension in the next round of amplification. In an adaptation of this procedure, simultaneous bi-directional sequencing of both strands of a double-stranded DNA may be performed using two strand-specific primers, each carrying a unique label. A variety of commercially available kits are available that provide appropriate reagents and instructions for carrying out such reactions using thermostable polymerase: SequiTherm Long-Read Cycle Sequencing Kit-LC (Cat # S36100LC), Epicentre Technologies, Madison, Wis., U.S.A.; SequiTherm Excel Long-Read DNA Sequencing Kit-LC (Cat. # SE610OLC), epicentre Technologies, Madison, Wis., U.S.A.; Thermo Sequenase fluorescent labelled primer cycle sequencing kit with 7-deaza-dGTP (Cat. #RPN 2438), Amersham Life Science, Cleveland, Ohio, U.S.A.; and, Circum Vent Thermal Cycle Sequencing Kit (Cat # 430-100), New England Biolabs, Beverly, Mass., U.S.A.

Mucosal disease (MD) is one of the most common viral diseases in cattle, causing significant economic loss. MD is characterized by fever, salivation, nasal discharge, diarrhoea, anorexia, dehydration, and abortion. The disease is caused by an RNA virus known as the bovine viral diarrhoea virus (BVDV). The sequences of several variants of the BVDV genome are known (Collett, M. S. et al., 1988, "Molecular Cloning and Nucleotide Sequence of the Pestivirus Bovine Diarrhoea Virus", Virology 165: 191–199; Pellerin et al., 1994, "Identification of a New Group of Bovine Viral Diarrhoea Virus Strains Associated with Severe Outbreaks and High Mortalities", Virolgogy 203: 260–268). BVDV belongs to a family of pestivirus which shares many similarities with viruses causing boarder disease and hog cholera. BVDV occurs in both non-cytopathogenic (ncp) and cytopathogenic (cp) strains. The ncp strain survives in animal tissues without any disruption as a latent invention. The cp strain causes cellular disruption and disease.

As a polymorphic RNA virus, BVDV is an example of the wide range of organisms for which reliable diagnostic protocols are required, and for which it would be desirable to have techniques for efficiently assaying polymorphisims that may be indicative of divergent pathologies associated with different strains of the organism. Efficient techniques for determining the evolutionary lineage of a particular pathogen, as evidenced by its complete or partial nucleic acid sequence, may also be useful in providing epidemiological information about the organism.

SUMMARY OF THE INVENTION

An object of the present invention is to provide methods for simultaneously analysing multiple nucleic acid regions in a single reaction. The methods may for example be adapted to analyse the sequences obtained from multiplexed amplification reactions. Such information may be useful for the reliable diagnosis and differentiation of pathological organisms. Such information may also be useful in genomic differentiation of individual by procedures commonly referred to as 'DNA fingerprinting'.

In one embodiment, the invention provides a method of sequencing a nucleic acid in a reaction mixture comprising first and second nucleic acid target sequences. The target sequences may be present on the same or different nucleic acid molecules. First and second labelled sequencing primers are provided that are hybridizable, respectively, to the first and second nucleic acid target sequences. The second sequencing primer being at least as long as the total length of the first sequencing primer plus the length of the first target sequence. The reaction mixture is provided with a DNA polymerase, deoxyribonucleotides, and a chain-terminating deoxyribonucleotide, under conditions that permit duplication of the first and second target sequences by the polymerase to proceed by extension from the first and second sequencing primers respectively. As in a typical Sanger sequencing reaction, the periodic incorporation of the chain-terminating nucleotide by the polymerase terminates polymerization to produce a pool of primer extension products of various lengths. In accordance with the invention, each of the primer extension products in the pool beginning with the second sequencing primer will be longer than the primer extension products in the pool beginning with the first sequencing primer. Once the sequencing reactions have been completed, the lengths of the primer extension products in the pool may be detected by known means, such as by gel electrophoresis.

The method of the invention may be adapted to work with additional nucleic acid target sequences. In such embodiments, additional labelled sequencing primers may be provided that are hybridizable to the additional target sequences. The additional sequencing primers being at least as long as the longest sequence in the pool of primer extension products.

One or more of the sequencing primers may be a 'tailed' sequencing primer comprising a portion that is non-homologous to the target nucleic acid sequences. The non-homologous portions of the tailed sequencing primer may be 5' to regions of the tailed sequencing primer that are hybridizable to the target sequences. In alternative embodiments, the 'tailed' portion of the sequencing primers may include non-linear DNA molecules, such as branched DNA or dendritic nucleic acids. Alternatively, non-DNA molecules may form the 'tail' of the sequencing primers, to provide the primers with an appropriate molecular weight for use in the methods of the invention.

The methods of the invention may include the step of amplifying the first and second nucleic acid target sequences using an amplification reaction. A variety of amplification reactions may be used, including a polymerase chain reaction. For example, the amplification reaction may comprises providing in the reaction mixture first and second double-stranded nucleic acid regions to be amplified, each comprising complementary strands having opposing 3' ends defining the region to be amplified. A first pair of amplification primers may be provided, a member of the first pair of amplification primers being hybridizable to each of the 3' ends of the complementary strands of the first region to be amplified. The first region to be amplified includes, or is the same as, the first nucleic acid target sequence which is to be the subject of the sequencing reaction of the invention. A second pair of amplification primers may be provided, a member of the second pair of amplification primers being hybridizable to each of the 3' ends of the complementary strands of the second region to be amplified. The second region to be amplified includes, or is the same as, the second nucleic acid target sequence which is to be at least partially sequenced. The reaction mixture is provided with a DNA polymerase, deoxyribonucleoside triphosphates and conditions that permit duplication by the DNA polymerase of the first and second regions to be amplified to proceed by extension from the first and second pairs of amplification primers respectively. As in a typical polymerase chain reaction, the nucleic acid regions may then be amplified by cycling the reaction mixture between a first temperature at which the complementary strands of the regions to be amplified melt, and a second temperature at which the amplification primers anneal to the 3' ends of the complementary strands of the regions to be amplified, and at which the polymerase catalyses duplication of the first and second regions to be amplified by extension from the first and second pairs of amplification primers respectively.

The sequencing and amplification reactions of the invention may be combined in a cycle sequencing reaction, wherein a member of the first and second amplification primer pairs is respectively the same as the first and second labelled sequencing primers.

In an alternative embodiment, the method of the invention further comprises a step of extending a sequence during amplification (which may be called 'step-up' amplification). In such an embodiment, a member of the first pair of amplification primers includes sequences hybridizable to the 3' end of one of the complimentary strands of the first region to be amplified. The step-up amplification primer also has additional sequences that are not hybridizable to the 3' end of that complementary strand. These additional sequences are utilized to extend the sequence during amplification.

The method of extending a sequence during amplification in accordance with the invention may include providing a reaction mixture comprising a double-stranded nucleic acid region to be amplified. The region to be amplified having first and second complimentary stands. The region to be amplified being defined by a 3' end on each of the first and second complimentary strands. A first amplification primer is provided having sequences complementary to the 3' end of the first complementary strand, and having additional sequences that are not complementary to the 3' end of the first complimentary strand. These additional sequences of the first amplification primer may be 5' to the sequences on the first amplification primer that are complementary to the target. A second amplification primer is provided having sequences complimentary to the 3' end of the second strand of the target sequence. The reaction mixture is provided with a DNA polymerase, deoxyribonucleoside triphosphates and conditions suitable for the polymerase to catalyse extension of the amplification primers. The region to be amplified is amplified and extending by cycling the reaction mixture between a first temperature at which the complementary strands of the target nucleic acid sequence melt, and a second temperature at which the amplification primers anneal to the 3' ends of the complementary strands and the polymerase catalyses extension from the amplification primers.

It will be appreciated that the methods of extending and amplifying a sequence may be adapted to work with series of primers, each having additional sequences, thereby further stepping-up the size of the region to be amplified. Building on the foregoing example, the region to be amplified may be further amplified and extended by providing a third amplification primer having sequences complementary to the additional sequences in the first amplification primer. The third amplification primer then further comprises 'supplementary' sequences that are not complementary to the first amplification primer or to the nucleic acid sequence to be amplified. These supplementary sequences form the basis for further extension of the region being amplified. The supplementary sequences may be 5' to the sequences on the third amplification primer that are complementary to the additional sequences on the second amplification primer.

DETAILED DESCRIPTION OF THE INVENTION

The invention provides a method of sequencing a nucleic acid, such DNA or RNA, having at least first and second regions to be sequenced. The regions to be sequenced may be found on the same nucleic acid molecule (or genome), or on different molecules in the same sample.

Sequencing primers are selected that are hybridizable under appropriate conditions to the regions which are to be sequenced, the primers annealing to the 3' end of the regions to prime polymerization. The primers are selected so that each produces a distinct set of fragments in the sequencing reaction. For example, the second of two primers would be selected to be at least as long as the total length of the first sequencing primer plus the length of the first region to be sequenced. In this way, the products of the sequencing reaction initiated at the second primer will always be longer than the products of the sequencing reaction initiated at the first primer.

Figure 1:
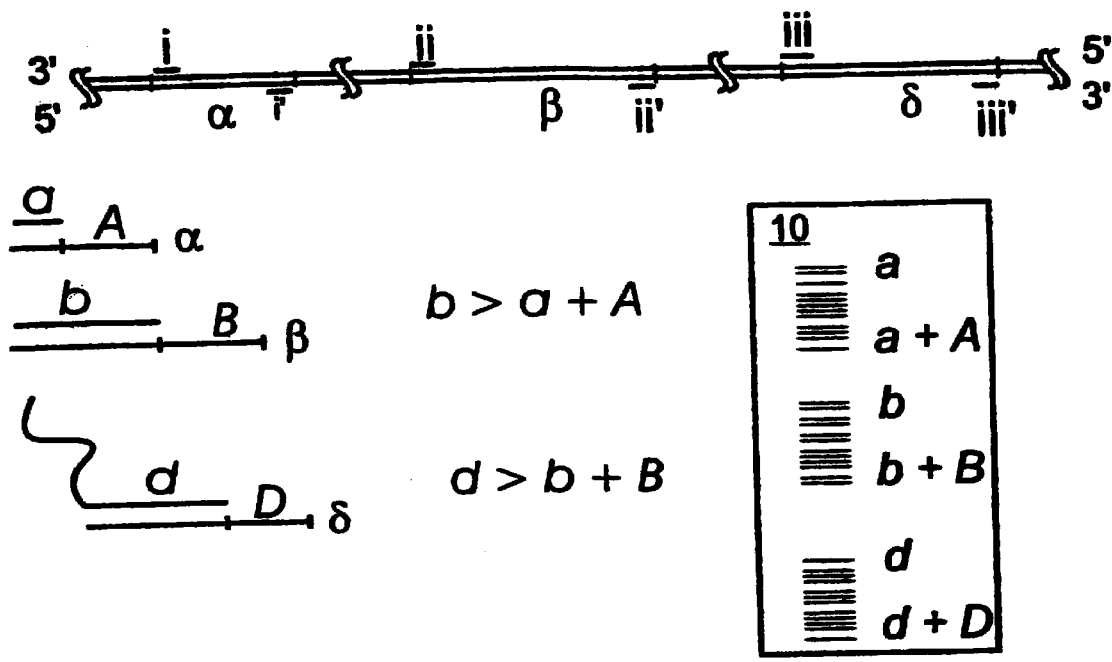
FIG. 1 is a schematic view of a multi-locus genomic analysis protocol, showing the analysis of three genomic regions: α,β, and δ. Each of the three regions is amplified using paired PCR primers, region α is amplified with primers i and i', region β is amplified with primers ii and ii', and region δ is amplified with primers iii and iii'. Once the regions α, β, and δ are amplified, they may be sequenced. Sequencing primer a is used to sequence segment A on region α, sequencing primer b is used to sequence segment B on region β, 'tailed' sequencing primer d is used to sequence segment D on region δ. The length of sequencing primer b is greater than the combined length of sequencing primer a plus segment A. The length of sequencing primer d is greater than the combined length of sequencing primer b plus segment B. A schematic illustration of a sequencing gel 10 is also shown.

The sequencing reaction may be carried out using known methods, by mixing the sequencing primers with the nucleic acid to be sequenced in the presence of polymerase, nucleotides and a chain-terminating nucleotide. Conditions are used that permit duplication of the regions of interest by the polymerase to be initiated from the sequencing primers. The periodic incorporation of the chain-terminating nucleotide terminates polymerization to produce a pool of sequences of various lengths. The selection of primers of an appropriate length dictates that each of the sequences in the pool beginning with one primer will be different in length from the sequences beginning with another primer. Appropriate conditions may be selected in certain embodiments for the use of sequencing primers that are preferably between 10 and 600 base pairs (bp) in length, or more preferably between 16 and 500 bp. For example, where there are two primers, with the second primer being longer than the combined length of the first primer and the first region sequenced from the first primer, all of the sequences produced from the second primer will be longer than the sequences in the pool beginning with the first primer. This differentiation of sequencing reaction product lengths is illustrated in FIG. 1 as a schematic sequencing gel 10. Additional regions may of course similarly be sequenced from primers that are longer than the products of the sequencing reaction from any other primer.

The length of the products of the sequencing reaction may be limited by choosing to sequence a nucleic acid of defined length. Restriction fragments (which may be subcloned using known techniques) or amplification products of defined length may, for example, be sequenced to produce a pool of sequencing reaction products that vary in length between, at a minimum, the length of the sequencing primer and, at a maximum, the length of the nucleic acid fragment being sequenced.

Figure 2:
FIG. 2 is a schematic diagram showing bidirectional sequencing with primers e and e' and the alternative use of sequencing terminator t. The $T_m$ of the terminator being higher than the Tm of primers e and e'.

Alternatively, the length of the sequencing reaction products may be limited by using a sequencing terminator comprising an oligonucleotide that hybridizes to the 3' end of the region to be sequenced, wherein the sequencing terminator has a 3' end from which polymerization may not be initiated, such as a 3' terminal ddNTP. FIG. 2 illustrates the alternative use of sequencing terminator t to define the length of sequencing reaction products extended from sequencing primer e. A terminator t could for example be a polynucleotide with a 3' dideoxy nucleotide, or any other nucleotide or other moity from which further 3' strand extension was not possible.

In effect, the use of sequencing primers of an extended length in accordance with the present invention increases the molecular weight of the primer extension products produced by a sequencing reaction, so that the sequencing reaction products from one primer are distinguishable from the sequencing reaction products of another primer. In alternative embodiments, the molecular weight of the sequencing primer extension products may similarly be altered, so that the primer extension products are distinguishable, by using sequencing primers with other chemical modifications. Alternative modifications include the use of known types of non-linear DNA molecules, such as branched DNA or dendritic nucleic acids. Branched DNA technologies are described, for example, in the following references: Cao Y, et al., 1995, "Clinical Evaluation of Branched DNA Signal Amplification for Quantifying HIV Type 1 in Human Plasma", AIDS Research and Human Retroviruses 11(3): 353–361; Collins M. L. et al., 1995, "Preparation and characterization of RNA standards for use in quantitative branched DNA hybridization assays", Analytical Biochemistry 226(1):120–129; Dewar R. et al., 1994, "Application of Branched DNA Signal Amplification to Monitor Human Immunodeficiency Virus Type 1 Burden in Human Plasma", Journal of Infectious Diseases 170:1172–1179. Dendritic nucleic acids are highly branched molecules that may be constructed by controlled hybridization and cross-linking of single-stranded nucleic acids, as described in the follwing references: Nilsen, T. W. et al., 1997, "Dendritic nucleic acid structures" J. Theor. Biol. 187(2): 273–84. An alternative approach is to modify the primers with phosphoramidite to increase their molecular weight appropriately. These alternative chemical modifications of the sequencing primers may be adapted to shift the apparent molecular weights of the sequencing reaction products so that the fragments beginning with one primer all have different apparent molecular weights than the sequencing reaction products beginning with other primers.

The sequencing primers are accordingly provided so that the apparent molecular weight on gel electrophoresis of a 'second' primer, is at least as great as the apparent molecular weight of an extended 'first' sequencing primer, i.e. the first sequencing primer extended to comprise a first target sequence, where the first and second sequencing primers hybridize respectively to first and second target sequences to facilitate sequence analysis of the targets.

The products of the sequencing reaction may be analysed in accordance with known sequencing techniques, such as by separating the sequences in the pool according to length and detecting the lengths of the sequences in the pool. Autoradiography of sequences produced from radiolabelled sequencing primers and separated on polyacrylamide gels is one such technique. Alternative methods include detecting fluorescently labelled sequencing reaction products separated by capillary gel electrophoreses.

In one aspect of the invention, only one chain-terminating nucleotide is used in the sequencing reaction. In this embodiment, sequence information is obtained for only one of the four nucleotides in the region of interest. An advantage of this approach is that it requires only a single sequencing reaction, the results of which may be assayed in a single detection procedure, such as a single lane on a polyacrylamide sequencing gel. This technique may be particularly useful where the usual sequence of the region is known and it is desired to determine whether the region contained in the sample of interest conforms to this known sequence. For example, it may be desirable to confirm that an amplification reaction has faithfully amplified a target sequence, to rule out the possibility of a falsely positive amplification reaction. Partial sequence information may also be useful to distinguish subsets of an organism of interest. For example, different variants of a pathogen such as a virus may be distinguished by partial sequencing, or allelic forms of a gene associated with a disease or predisposition to disease.

In an alternative embodiment, bidirectional sequencing of the regions of interest may be used, as illustrated in FIG. 2. Bi-directional sequencing primers e and e' are shown in FIG. 2 bracketing region E that is to be sequenced. In a variant of the invention, where the bidirectional sequencing reactions are carried out with distinguishable labels, such as fluorescently labelled primers that absorb or emit at different wavelengths, then a single lane on a sequencing gel may be used to run out the sequencing reaction products from the two bidirectional sequencing reactions. These techniques may be applied in accordance with the invention to multiple regions of interest.

In one aspect of the invention, the regions to be sequenced may first be amplified. The polymerase chain reaction may for example be used to amplify regions for sequencing. The region to be sequenced may comprise all or only part of the amplified sequences. If only part of the amplified region is to be sequenced, the sequencing primers will be nested within the amplified regions. If the whole amplified region is to be sequenced, the sequencing primers may be selected from the amplification primers, one sequencing primer being selected for each of the amplified regions. FIG. 1 schematically illustrates a multi-locus genomic analysis protocol in accordance with this aspect of the invention, showing the analysis of three genomic regions: $\alpha$, $\beta$, and $\delta$. Each of the three regions in this embodiment is amplified using paired PCR primers: region $\alpha$ is amplified with primers i and i', region $\beta$ is amplified with primers ii and ii', and region $\delta$ is amplified with primers iii and iii'. Once the regions $\alpha$, $\beta$, and $\delta$ are amplified, they may be sequenced. In the illustrated embodiment, sequencing primer a is used to sequence segment A on region $\alpha$, sequencing primer b is used to sequence segment B on region $\beta$, 'tailed' sequencing primer d is used to sequence segment D on region $\delta$. As schematically shown in FIG. 1 by the formula "b>a+A", the length of sequencing primer b is greater than the combined length of sequencing primer a plus segment A. Similarly, as shown in FIG. 1 by the formula "d>b+B", the length of sequencing primer d is greater than the combined length of sequencing primer b plus segment B. A schematic illustration of a sequencing gel 10 is also shown, showing the fragments generated from the sequencing of region $\alpha$ as the bands between a and a+A, the fragments generated from the sequencing of region $\beta$ are shown as the bands between b and b+B, the fragments generated from the sequencing of region $\delta$ are shown as the bands between d and d+D.

Methods for conducting PCR are described, for example, in Innis et al. (eds) 1995 "PCR Strategies", Academic Press, Inc. San Diego; and Erlich (ed), 1992, "PCR Technology", Oxford University Press, New York, both of which are hereby incorporated by reference. Generally PCR amplification occurs in a buffered aqueous solution, preferably at pH of 7–9, most preferably about 8. The primer pair(s) is(are) added in suitable amounts (at a suitable molar ratio to the target). Deoxyribonucleoside triphosphates dATP, dCTP, dGTP and dTTP are also added to the synthesis mixture in adequate amounts and the resulting solution is heated to about 85° C.–100° C. for about 1 to 10 minutes, preferably from 1 to 4 minutes. After this heating, the solution is allowed to cool, generally to about 20° C.–40° C., i.e. a temperature appropriate for primer hybridization. Polymerization is initiated in the cooled mixture, typically by adding an enzyme such as DNA polymerase. Suitable enzymes for this purpose may include in particular embodiments, for example, $E.\ coli$ DNA polymerase I, Klenow fragment of $E.\ coli$ DNA polymerase I, $T_4$ DNA polymerase or other DNA polymerases, reverse transcriptase or other enzymes including heat stable enzymes which will facilitate a combination of the deoxyribonucleoside triphosphates in the proper manner to form primer extension products which are complementary to each nucleic acid strand template. Generally, the synthesis will be initiated at the 3' end of the primer and proceed along the template strand until synthesis terminates. The newly synthesized complementary strands form the templates used in the succeeding step of the amplification process. In the next step, the complementary strands are separated, as described above, to provide single-stranded molecules to which primers are hybridized for strand extension. The steps of strand separation and extension may be repeated as often as is necessary to produce the desired quantity of the target nucleic acid sequence. The amount of the target nucleic acid sequence produced will thereby accumulate in exponential fashion.

Appropriate conditions for amplification may be established by those of skill in the art of the invention in accordance with known techniques. For example, in some embodiments, appropriate conditions may comprise: 0.2 mM dNTP, 2.2 mM MgCl$_2$, 50 mM KCl, 10 mM Tris-HCl pH 9.0, 0.1% Triton X-100.

Appropriate amplification primers may be selected for a particular analysis in accordance with the invention using criteria known in the art, such as the criteria outlined in the general amplification references referred to above. For PCR amplification, the primers are generally designed so that the position at which each primer hybridizes along a target duplex sequence is such that an extension product synthesized from one primer, when separated from the template serves as a template for the extension of the other primer. Typically, the amplification primers are from about 10 to about 30 nucleotides in length, more typically from about 14 to about 24 nucleotides in length. In 'cycle-sequencing' reactions and 'step-up' amplification reactions in accordance with the present invention, it may however be preferable to use longer primers.

Alternative methods of amplifying sequences may also be used in accordance with various aspects of the present invention. For example, appropriate methods may be adapted by those skilled in the art from the following techniques: strand displacement amplification (see, e.g. Persing et al. (eds) "Diagnostic Molecular Microbiology: Principles and Applications", American Society for Microbiology, Washington, D.C.); The Ligase Chain Reaction (see, e.g. Wu (1989) Genomics 4:560, or Landegrin (1988) Science 241:1077, or Barringer (1990) Gene 89:117); Transcription-Based Amplification (see, e.g. Kwoh Proc. Natl. Acad. Sci. U.S.A., 86:1173 (1989)); Self-Sustained Sequence Replication (see Guatelli (1990) Proc. Natl. Acad. Sci. U.S.A., 87:1874); Q Beta Replicase Amplification; or other RNA Polymerase Mediated Techniques (e.g. NASBA, Cangene Corporation, Mississauga, Ontario). Alternative references that may be of use to those of skill in the art for carrying out such processes in accordance with the invention are as follows: Berger and Kimmel, "Guide to Molecular Cloning Techniques", Methods in Enzymology 152:307–316, Academic Press, Inc., San Diego, Calif. U.S.A; Sambrook et al. (1989) "Molecular Cloning—A Laboratory Manual (2nd Ed.) Vol. 1–3, Cold Spring Harbour Laboratory, Cold Spring Harbour Press, New York.

Isolation of nucleic acids from biological sources for analysis in accordance with the present invention may be carried by any of a variety of known means or equivalents or improvements thereon. For example, methods are described in Rothbart et al. (1989), "PCR Technology", Stockton Press, New York and Han et al. (1987) Biochemistry 26:1617–1625. Commercially available kits may also be conveniently used for this purpose in accordance with the instructions provided by their manufacturers, such as kits may be available from the following manufacturers: Invitrogen, San Diego, Calif. U.S.A.; Stratagene, La Jolla, Calif. U.S.A.

Figure 3:
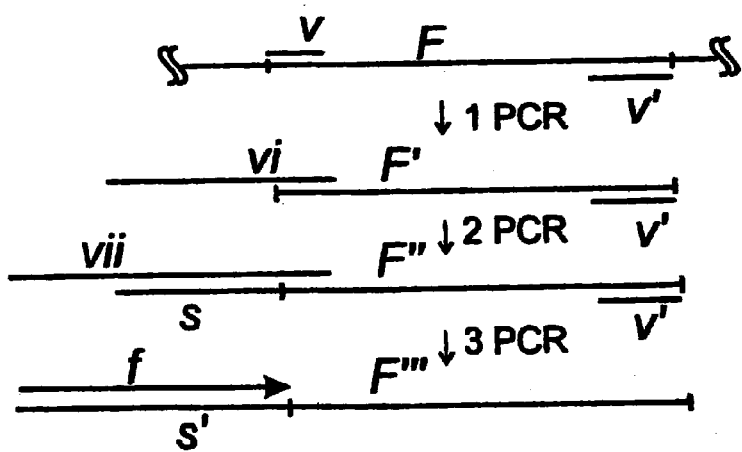
FIG. 3 is a schematic diagram showing 'step-up' amplification of segment F for sequencing with sequencing primer f The first round of amplification uses PCR primers v and v' to produce polynucleotide F', the second round of amplification uses sequencing primers vi and v' to produce polynucleotide F", the third round of amplification uses PCR primers vii and v' to produce polynucleotide F'''.

In alternative embodiments, as shown in FIG. 3, the invention utilizes a 'step-up' amplification protocol to increase the length of the region that will be subjected to sequence analysis. This 'step-up' amplification may be useful to produce a synthesized region, shown as s and s' in FIG. 3, that is at one (as illustrated) or both (not illustrated) ends of the genomic region of interest, shown as F, F', F" and F'" in FIG. 3, through successive iterations of amplification, shown as 1 PCR, 2 PCR and 3 PCR. The linear representation of the molecule to be amplified is shown by one line in FIG. 3 for simplicity, in practice a double stranded molecule would generally be the substrate for amplification, as would be the case in a standard PCR reaction. As shown in FIG. 3, the first round of amplification uses amplification primers v and v' to produce polynucleotides consisting of region F'. The second round of amplification (shown as 2 PCR in FIG. 3) uses sequencing primers vi and v' to produce polynucleotides comprising region F" and newly synthesized region s, which corresponds to the region of the vi primer that is not complementary to the F' region. The third round of amplification, 3 PCR, uses PCR primers vii and v' to produce polynucleotides comprising region F'" and synthetic region s' which consists of regions complementary to amplification primers vi and vii. The step-up amplification may be used to create synthetic regions at one end of the region of interest, as illustrated in FIG. 3, or at both ends with the appropriate adaptation of the procedure shown in FIG. 3. The utilization of step-up amplification to produce one or more synthetic regions s for hybridization to a sequencing primer f may be useful as an alternative to the use of 'tailed' sequencing primers, such as d, or where the sequence of the genomic region 5' or 3' to the region of interest, such as 5' to F in FIG. 3, is not known. Step-up amplification at both ends of a region facilitates the use of amplification primer pairs with sequentially increasing $T_m$s.

In one embodiment, a step-up amplification of a portion of the BVDV genome (sequences 6941 to 7255 of the BVDV genome) may be performed using the following amplification primer sets. In one embodiment, 'cycle-sequencing' (simultaneous amplification and sequencing reactions, i.e. amplification in the presence of one ddNTP and a labelled primer) could be preformed using one member of Primer Set 3 as a labelled sequencing primer:

Primer Set 1:

5'-GTA GGT AGA GTG AAA CCC GG-3' (SEQ ID NO: 1)

(complimentary to sequences 6941–6961 of the BVDV genome, and analogous to amplification primer v in FIG. 3)

5'-CGG GAC CTG GAC TTC ATA GC-3' (SEQ ID NO: 2)

(complimentary to sequences 7255–7245 of the BVDV genome)

Primer Set 2:

5'-$(dG)_{30}$GTA GGT AGA GTG AAA CCC GG-3' (SEQ ID NO: 3)

(analogous to amplification primer vi in FIG. 3)

5'-$(dG)_{30}$ CGG GAC CTG GAC TTC ATA GC-3' (SEQ ID NO: 4)

Primer Set 3:

5'-$(dA)_{30}(dG)_{30}$GTA GGT AGA GTG AAA CCC GG-3' (SEQ ID NO: 5)

(analogous to amplification primer vii in FIG. 3)

5'-$(dA)_{30}(dG)_{30}$ CGG GAC CTG GAC TTC ATA GC-3' (SEQ ID NO: 6)

In another aspect of the invention, the step-up amplification primers are chosen so that the melting point of the primer used in each successive amplification is higher then in the preceding amplification. The primer pair with the lowest $T_m$ may be added first, and primer pairs with higher $T_m$s may be added sequentially. In this way, each extension reaction may be carried out at a sufficiently high temperature to prevent the primer used in the preceding amplification reaction from annealing. This allows successive step-up amplification reactions to be carried out without an intervening step of removing amplification primers from previous amplification reactions, while helping to ensure that amplification takes place in each step only from the most recently added amplification primer. For example, in FIG. 3, the melting point of primers would be in the order v<vi<vii.

In another alternative embodiment, each of the successive step-up amplification primers may be added to the amplification reaction at the outset, with the second and subsequent primers encapsulated in materials, such as wax, with increasing melting temperatures. In this way, when it is desired to release the next of the primers, the reaction mixture may be raised to the next higher temperature at which that primer will be released. This procedure avoids the necessity of adding successive primers to the reaction mixture during amplification.

In one aspect of the invention, one or more of the sequencing primers may include regions that are not homologous to the region to be sequenced from that primer. Primers of this sort may be known as 'tailed' sequencing primers. The non-homologous regions of a tailed primer may be located at the 5' end of the primer, so that the homologous 3' end of the primer anneals to the region of interest in order to prime polymerization, as shown in FIG. 1 for sequencing primer d. In alternative embodiments, the non-homologous portion of the tailed primer may be situated between the 3' end of the primer which is homologous to the region of interest and a 5' region of the tailed primer which is also homologous to the region of interest. Any arrangement of non-homologous sequences in a 'tailed' primer may be acceptable (which may of course thereby have mismatching segments that do not literally form a 'tail'), provided that the primer remains capable of initiating polymerization of the region of interest. The presence of non-homologous sequences in the tailed primer will affect the melting temperature of the primer and thereby influence the conditions under which the sequencing reaction is performed, as determined in accordance with sequencing primer hybridization parameters known in the art.

The use of the sequencing methods of the present invention may usefully be combined with nucleic acid amplification techniques to reduce the occurrence of false-positive results from the amplification reactions. For example, PCR (which may be preceded by reverse transcription for RNA viruses, i.e. production of a cDNA copy using an RNA molecule as template and an oligonucleotide as primer, which may be abbreviated as "RT PCR") may be used to detect the presence of a target nucleic acid in a sample, such as a viral nucleic acid. This approach has the well recognized advantage of being able to detect very small amounts of the target nucleic acid. However, the amplification reaction can generate false positive results when non-target nucleic acids are erroneously amplified. The reliability of the amplification assay may be enhanced by amplifying more than one target on a nucleic acid of interest, such as two regions of a viral genome, one such procedure is known as multiplexed PCR. However, false positive results may still occur in the event of non-specific amplification of more than one region. The sequencing methods of the present invention may be used to detect the occurrence of such false-positive results by providing a partial or complete sequence of the amplified regions. The sequencing methods of the present invention are accordingly specifically adapted to be carried out on at least two non-homologous regions simultaneously, using a single sequencing reaction.

The sequence data generated by the methods of the present invention may be useful to provide information about the sub-type of an organism. For example, the presence of a target nucleic acid from the organism in a sample may be indicated by a positive amplification reaction, and the reliability of that detection may be verified by sequencing in accordance with the present invention. The sequence information thus generated may vary from one sub-type of the target organism to another. For example, viral nucleic acids often exhibit significant variability from one strain to another, particularly RNA viruses such as HIV. Amplification primers may be selected for detecting a wide range of such strains by selecting primers homologous to sequences that are generally conserved amongst all strains of the organism. Variation between strains may then be assayed by assessing the sequence data generated in accordance with the invention.

EXAMPLE 1

This example discloses an aspect of the present invention useful for the detection of bovine viral diarrhoea virus (BVDV). The methods of this example may be adapted for detection and differentiation of nucleic acids from other organisms, such as other RNA viruses.

In this example, a two dye system is used for sequence analysis. In this system, two lasers are used to detect the labelled products of the sequencing reaction. One laser excites at a wavelength of 700 nm and the other at 800 nm. Sequencing reaction primers are labelled with two different near-infrared fluorescent dyes (such as those available from LI-COR, Inc. of Lincoln, Nebr., U.S.A.), one of which responds to illumination by the 700 nm laser, that dye being designated IRD700, the other dye responding to the 800 nm laser and being designated IRD800. Using this system, two different DNA fragments of the same molecular size produced by different sequencing reactions, and hence each labelled with different dyes, may be distinguished by their emission under laser illumination at the alternative wavelengths. Dye-labelled DNA fragments may automatically be detected during electrophoresis by a scanning fluorescence microscope. The two primer sets used in this example are:
Primer set 1
[Labelled IRD 700] 5'GTA GGT AGA GTG AAA CCC GG (SEQ ID NO: 1)
(Which hybridizes to a first strand of the BVDV genome at positions 6941–6961)
[Labelled IRD 800] 5' CGG GAC CTG GAC TTC ATA GC (SEQ ID NO: 2)
(Which hybridizes to the complementary strand of the BVDV genome at positions 7255–7235)
Primer set 1 amplifies a region of 314 base pairs, i.e. from position 6941 to position 7255.
Primer set 2
[Labelled IRD 700] 5'(dG)$_{300}$ AGG CTA GCC ATG CCC TTA GT (SEQ ID NO: 7)
(Which hybridizes to the BVDV genome at positions 99–118)
[Labelled IRD 800] 5' (dG)$_{300}$ TCT GCA GCA CCC TAT CAG G (SEQ ID NO: 8)
(Which hybridizes to the complementary strand of the BVDV genome at positions 324–342)
Primer set 2 amplifies a region of 243 base pairs, i.e. from position 99 to position 342, and a synthetic sequence of 300 bp at each end, for a total length of the whole fragment of 843.

In this example, genomic analysis is carried out as follows:
1. Preparation of Total RNA
Total RNA was extracted using the TRIZOL™ reagent and methods for its use recommended by the manufacturer, Life Technologies, Inc., Gaithersburg, Md., U.S.A. Alternatively, total RNA may be prepared by any suitable method known to those skilled in the art (an alternative kit is the RNA Isolation Kit available from Stratagene Corp. of La Jolla, Calif., USA; see also Chomczynski, et. al. (1987) Analytical Biochemistry 162, 156. "Single Step Method of RNA Isolation by Acid Guanidinium Thiocyanate-Phenol-Chloroform Extraction."). A method in accordance with one embodiment is as follows:

a. 250 µl of the cell suspension was added to 750 µl of Trizol reagent b. Left at room temperature for 5 minutes.

c. 200 µl of chloroform was added and mixed well for 15 sec d. The mixture was centrifuged at 12800 rpm at +4° C. for 10 minutes e. The upper aqueous layer was transferred into a new 1.5 ml Eppendorf tube.

f. 500 µl of isopropanol was added and mixed.

g. Left at room temperature for 5 minutes.

h. The mixture was centrifuged at 12800 rpm at +4° C. for 10 minutes.

i. The supernatant was discarded and 200 µl of 85% alcohol was added.

j The mixture was centrifuged at 12800 rpm at +4° C. for 10 minutes k The supernatant was discarded and the tubes were air dried.

l. Total RNA was suspended in 20 µl of diethylpyrocarbonate (DEPC) treated water.

2. Preparation of cDNA cDNA may be prepared from isolated RNA in accordance with methods well known in the art. One embodiment is as follows:

a. The following were mixed in a 1.5 ml centrifuged tube:
Total RNA 1 µg 2 µl;
Down stream primer (10 pM/ml) 2 µl;
Water 8 µl.

b. The mixture was heated at 70° C. for 10 minutes.

c. To the heated mixture, the following were added:
5× 1st strand synthesis buffer 4 µl;
dNTP(10 mM) 1 µl 0.1 MDTT 2 µl;

d. The mixture was heated at 42° C. for 2 min.

e. 1 µl of SUPERSCRIPT II (a reverse transcriptase available from Life Technologies, Inc., Gaithersburg, Md., U.S.A.) was added to the above mixture.

f. Incubated at 42° C. for 50 minutes.

g. The reaction was stopped by heating at 70° C. for 10 min.

3. Amplification of specific regions

Amplification of cDNA may be undertaken by any suitable method known to those in the art. In the embodiment of this example, the method was as follows:

Using 2 µl of the reverse transcription mixture, two regions of the cDNA were amplified on a GeneAmp™ 2400 thermocycler using the primer pairs identified in this example, in accordance with methods specified by the manufacturer, The Perkin-Elmer Corporation:

a. The reaction was carried out in 25 µl of reaction mixture as follows:
$dH_2O$ 16.0 µl
Template 2.0 µl b. The mixture was heated to 95° C. for 10 minutes c. The master mix was prepared as follows:
Primer 1 (10 pmol/µl) 5 µl
Primer 2 (10 pmol/µl) 5 µl
dNTP (10 mM) 2.5 µl
10× Buffer 2.5 µl
$MgCl_2$ 25 mM 7.5 µl
Taq 5U/µl 2.5 µl
7.0 µl of master mix was added d. PCR may be carried out in a GeneAmp™ 2400 thermocycler (The Perkin-Elmer Corporation) in accordance with the manufacturer's instructions.

4. Purification of PCR products

Optionally, to separate the amplification products from the unreacted primers, gel filtration may be used. In this example, the amplified material is purified using Sephadex™ G-50 gel filtration media (available from Sigma Chemical, St. Louis, Mo., USA). Other methods known in the art may be used to purify the amplification products, or this step may be omitted.

5. Sequencing

The amplified segment(s) may be cycle-sequenced using labelled (flourescent) primer sets 1 and 2 for bi-directional multi-locus cycle-sequencing. In each set of primers, one primer is labelled with a fluorescent dye that absorbs at 700 nm and the other primer is labelled with fluorescent dyes that absorb at 800 nm. In this embodiment, only one dideoxynucleotide is used (single tract sequencing). Alternatively, four tubes could be prepared, one with each of the four possible dedioxynucleotides, to obtain a full sequence.

Cycle sequenced products are separated on 0.25 mm thick 6% polyacylamide gel at 1500 volts on an automated sequencer (LI-COR Inc., Lincoln, Nebr., USA).

The single tract sequence may be analysed using appropriate computer software and compared with a BVDV DNA sub-type data bank. This analysis may be used to identify the subtype of BVDV in the sample.

EXAMPLE 2

This example provides for the analysis of four regions of the BVDV genome using primers of different molecular weights and using different fluorescnt labels. In this embodiment, a two dye sequencing system, as described in Example 1, may be used to resolve comigrating sequencing reaction products from primer sets 1 and 2, and to resove comigrating sequencing reaction products from primer sets 3 and 4, while extension products from both sets 1 and 2 will be resolved by molecular weight from the extension products of primer sets 3 and 4. In this example, the following primers are used:

Primer set 1

[Labelled IRD 700] 5' GTA GGT AGA GTG AAA CCC GG (SEQ ID NO: 1)

(Which hybridizes to a first strand of the BVDV genome at positions 6941–6961)

[Un labelled] 5' CGG GAC CTG GAC TTC ATA GC (SEQ ID NO: 2)

(Which hybridizes to the complementary strand of the BVDV genome at positions 7255–7235)

Primer set 1 amplifies a region of 314 base pairs, i.e. from position 6941 to position 7255.

Primer set 2

[Labelled IRD 800] 5'AGG CTA GCC ATG CCC TTA GT (SEQ ID NO: 9)

(Which hybridizes to the BVDV genome at positions 99–118)

[Unlabelled] 5'TCT GCA GCA CCC TAT CAG G (SEQ ID NO: 10)

(Which hybridizes to the complementary strand of the BVDV genome at positions 7255–7235)

Primer set 2 amplifies a region of 243 base pairs, i.e. from position 99 to position 342.

Tailed Primer set 3

[Labelled IRD 700] 5'(dG)$_{300}$ GCA GAT TTT GAA GAA AGA CA (SEQ ID NO: 11)

(Which hybridizes to the BVDV genome at positions 4937–4960)

[Unlabelled] 5'(dG)$_{300}$ TTG GTG TGT GTA AGC CCA (SEQ ID NO: 12)

(Which hybridizes to the complementary strand of the BVDV genome at positions 5591–5609)

Tailed Primer set 4

[Labelled IRD 800] 5'(dG)$_{300}$ ACG TGG ACG AGG GCA TGC CC (SEQ ID NO: 13)

(Which hybridizes to the BVDV genome at positions 234–253)

[Unlabelled] 5'(dG)$_{300}$ TGT GCC ATG TAC AGC AGA GA (SEQ ID NO: 14)

(Which hybridizes to the complementary strand of the BVDV genome at positions 365–384)

Genomic analysis may be carried out using known methods in accordance with the similar methods disclosed in Example 1, or known alternatives to those methods.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

What is claimed is:

1. A method of sequencing a nucleic acid comprising:
   (a) providing in a reaction mixture first and second nucleic acid target sequences;
   (b) providing in the reaction mixture first and second labelled sequencing primers hybridizable respectively to the first and second nucleic acid target sequences, the second sequencing primer being at least as long as the total length of the first sequencing primer plus the length of the first target sequence;
   (c) providing in the reaction mixture a DNA polymerase, deoxyribonucleotides, a chain-terminating deoxyribonucleotide, and conditions that permit duplication of the first and second target sequences by the polymerase to proceed by extension from the first and second sequencing primers respectively, wherein the periodic incorporation of the chain-terminating nucleotide by the polymerase terminates polymerization to produce a pool of primer extension products of various lengths, each of the primer extension products in the pool beginning with the second sequencing primer being longer than the primer extension products in the pool beginning with the first sequencing primer; and,
   (d) differentiating the primer extension products based on differences of molecular weight;
   wherein at least one nucleic acid sequence, or at least one portion of a nucleic acid sequence, is determined.

2. The method of claim 1, further comprising the step of amplifying the first and second nucleic acid target sequences using an amplification reaction carried out prior to or simultaneously with said duplication of the first and second target sequences.

3. The method of claim 2, wherein the amplification reaction is a polymerase chain reaction.

4. The method of claim 2 wherein the amplification reaction comprises:
   (a) providing in the reaction mixture first and second double-stranded nucleic acid regions to be amplified, each comprising complimentary strands having opposing 5' ends defining the region to be amplified;
   (b) providing in the reaction mixture a first pair of amplification primers, a member of the first pair of amplification primers being hybridizable to each of the 5' ends of the complimentary strands of the first region to be amplified, the first region to be amplified comprising the first nucleic acid target sequence;
   (c) providing in the reaction mixture a second pair of amplification primers, a member of the second pair of amplification primers being hybridizable to each of the 5' ends of the complimentary strands of the second region to be amplified, the second region to be amplified comprising the second nucleic acid target sequence;
   (d) providing in the reaction mixture a DNA polymerase, deoxyribonucleoside triphosphates and conditions that permit duplication by the DNA polymerase of the first and second regions to be amplified to proceed by extension from the first and second pairs of amplification primers respectively;
   (e) amplifying the nucleic acid regions by cycling the reaction mixture between a first temperature at which the complimentary strands of the regions to be amplified melt, and a second temperature at which the amplification primers anneal to the 5' ends of the complimentary strands of the regions to be amplified and at which the polymerase catalyses duplication of the first and second regions to be amplified by extension from the first and second pairs of amplification primers respectively.

5. The method of claim 4 further comprising a cycle sequencing reaction wherein a member of the first and second amplification primer pairs is respectively the same as the first and second labelled sequencing primers.

6. The method of claim 4 further comprising the step of extending a sequence during amplification wherein a member of the first pair of amplification primers comprises a sequence hybridizable to a 3' end of the first region to be amplified, and a sequence not hybridizable to the complementary strands, the sequence that is not hybridizable to the complementary strands being 5' with respect to the hybridizable sequence of the amplification primer.

7. The method of claim 1 further comprising the step of separating the sequences in the pool according to length by gel electrophoresis.

8. The method of claim 1 wherein the first and second target nucleic acid sequences are present on different nucleic acid molecules.

9. The method of claim 1 wherein the reaction mixture is further provided with:

(a) an additional nucleic acid target sequence; and, (b) an additional labelled sequencing primer hybridizable to the additional target sequence, the additional sequencing primer being at least as long as the longest sequence in the pool of primer extension products.

10. The method of claim 1 wherein at least one of the sequencing primers is a tailed sequencing primer comprising a portion that is non-homologous to the target nucleic acid sequences.

11. The method of claim 10 wherein the tailed sequencing primer comprises first and second regions, the first region being hybridizable to a first region of the target nucleic acid sequence, and the second region, which is not hybridizable to the target nucleic acid sequence, being located 5' with respect to the first priming region.

12. A method of sequencing a nucleic acid comprising (a) providing in a reaction mixture first and second nucleic acid target sequences;

(b) providing in the reaction mixture first and second labelled sequencing primers hybridizable respectively to the first and second nucleic acid target sequences, the second sequencing primer having an apparent molecular weight on gel electrophoresis at least as great as the apparent molecular weight of the first sequencing primer when the first sequencing primer is extended to comprise the first target sequence;

(c) providing in the reaction mixture a DNA polymerase, deoxyribonucleotides, a chain-terminating deoxyribonucleotide, and conditions that permit duplication of the first and second target sequences by the polymerase to proceed by extension from the first and second sequencing primers respectively, wherein the periodic incorporation of the chain-terminating nucleotide by the polymerase terminates polymerization to produce a pool of primer extension products of various lengths, each of the primer extension products in the pool beginning with the second sequencing primer having an apparent molecular weight on gel electrophoresis at least as great as the apparent molecular weight of the primer extension products in the pool beginning with the first sequencing primer, and, (d) differentiating the primer extension products based on differences of molecular weight;

wherein at least one nucleic acid sequence, or at least one portion of a nucleic acid sequence, is determined.

* * * * *